United States Patent [19]

Jackson

[11] Patent Number: 5,279,594
[45] Date of Patent: Jan. 18, 1994

[54] INTUBATION DEVICES WITH LOCAL ANESTHETIC EFFECT FOR MEDICAL USE

[76] Inventor: Richard R. Jackson, One Atlantic Ave., Swampscott, Mass. 01907

[21] Appl. No.: 527,593

[22] Filed: May 23, 1990

[51] Int. Cl.$^5$ .................... A61M 5/32; A61M 25/00
[52] U.S. Cl. ................................. 604/265; 604/93; 623/12
[58] Field of Search ............... 604/96–103, 111, 112, 209, 264, 280; 623/1, 12

[56] References Cited

U.S. PATENT DOCUMENTS

| | | | |
|---|---|---|---|
| 4,421,333 | 4/1984 | Greco et al. | 623/12 |
| 4,560,720 | 12/1985 | Aoyagi et al. | 604/96 |
| 4,581,028 | 4/1986 | Fox, Jr. et al. | 604/265 |
| 4,867,968 | 9/1989 | Allen | 604/264 |
| 4,879,135 | 11/1989 | Greco et al. | 623/12 |
| 4,917,686 | 4/1990 | Bayston et al. | 604/265 |
| 4,977,894 | 12/1990 | Davies | 604/96 |
| 4,997,440 | 3/1991 | Dumican | 623/1 |

OTHER PUBLICATIONS

Gebelein, Charles editor, *Polymeric Materials and Artificial Organs;* American Chemical Society, pp. 15–18; 1984.
Bruck, Stephen, *Blood Compatible Synthetic Polymers;* Charles C. Thomas, pp. 23–24, 1974.
*American Heritage Dictionary*, 2nd edition, 1982, pp. 106, 108, 442, 1262.
*The Merck Index*, ninth edition, 1976, pp. 3001 and 5331.

*Primary Examiner*—C. Fred Rosenbaum
*Assistant Examiner*—Chalin Smith
*Attorney, Agent, or Firm*—Fish & Richardson

[57] ABSTRACT

A compound with topical anesthetic properties is incorporated in polymeric material making up the wall of a tube of intubation devices for introduction into body passages of an animal. A hydrophobic anesthetic compound is used which is more soluble in the polymeric wall material of the tube than in water. Because of the hydrophobic properties of the anesthetic compound, a quantity of anesthetic compound can be stored in solution in the polymeric wall material of the tube and this stored anesthetic compound is not washed out by the aqueous fluid which is present in the body passage. As a result, the anesthetic compound is transferred only to the contiguous tissue of the body passage and not disseminated systemically through the aqueous fluids. When the tube is in place within a body passage the anesthetic compound diffuses to the surface of body tissue touched by the tube where its anesthetic effect suppresses discomfort and undesired rejection reactions. Since the anesthetic compound is thus dispensed only to the contiguous tissue of the body passage, the quantity of anesthetic compound stored in the tube wall is sufficient to maintain effective anesthesia of the body passage for hours or days, and undesired effects of a general dissemination through the body are avoided.

11 Claims, 1 Drawing Sheet

INTUBATION DEVICES WITH LOCAL ANESTHETIC EFFECT FOR MEDICAL USE

BRIEF SUMMARY OF THE INVENTION

The invention relates to intubation devices which are introduced into body passages of human and non-human animals in certain medical procedures.

When conventional intubation devices are introduced into body passages in connection with medical procedures they cause discomfort and often elicit ejection reactions such as coughing or gagging by the patient which interfere with the procedure and may be injurious to the patient. An object of the invention is to provide in an intubation device a tube which dispenses a topical anesthetic to contiguous tissue in the body passage so as to reduce or eliminate the discomfort and undesired reactions.

According to the invention, a compound with topical anesthetic properties is incorporated in the polymeric material making up the wall of a tube. While the tube is in place within a body passage the anesthetic compound diffuses to the surface of body tissue touched by the tube where its anesthetic effect suppresses the discomfort and undesired rejection reactions. A hydrophobic anesthetic compound is used which is more soluble in the polymeric wall material of the tube than in water. Because of the hydrophobic properties of the anesthetic compound, a quantity of anesthetic compound can be stored in solution in the polymeric wall material of the tube and this stored anesthetic compound is not washed out by the aqueous fluid which is present in the body passage. As a result, the anesthetic compound is transferred only to the contiguous tissue of the body passage and not disseminated systemically through the aqueous fluids. Since the anesthetic compound is thus dispensed only to the contiguous tissue of the body passage, the quantity of anesthetic compound stored in the tube wall is sufficient to maintain effective anesthesia of the body passage for hours or days, and undesired effects of a general dissemination through the body are avoided.

DETAILED DESCRIPTION

Figure 1:
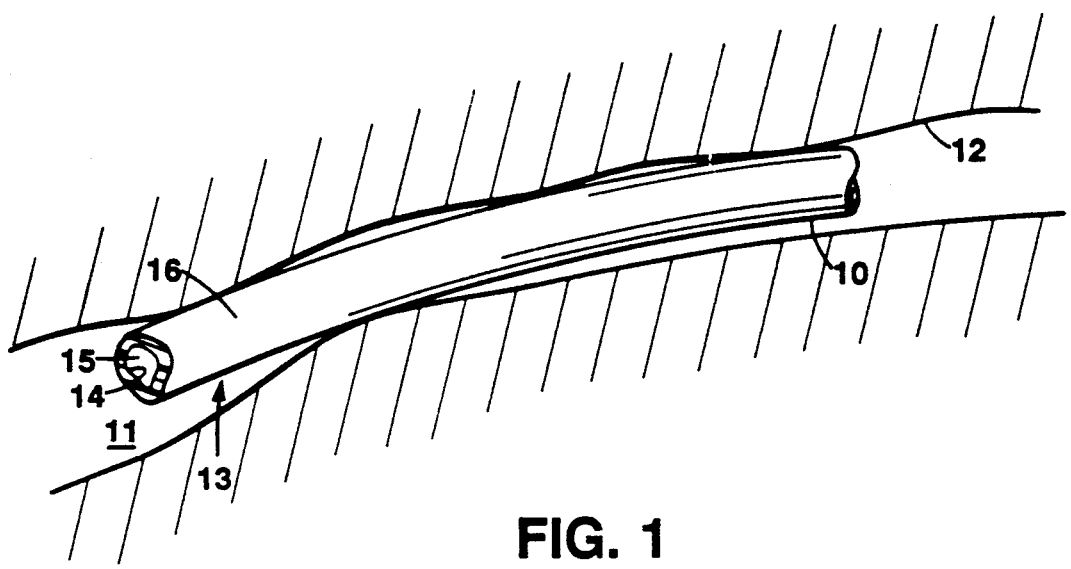
FIG. 1 shows a portion of a tube according to the invention emplaced in a body passage of an animal.

As shown in FIG. 1, an intubation device including tube 10, according to the invention, is emplaced within body passage 11. Tube 10 has a wall 13 with an inner surface 14 defining a lumen 15 and an outward facing surface 16 which contacts body tissue 12.

Wall 13 is composed of a organic polymeric wall material which may advantageously be polyvinyl chloride or vinyl-urethane copolymer. Dimensions of tube 10 are those conventionally used in intubation devices and may vary depending on the particular service of the device. A topical anesthetic compound is incorporated in the wall material of tube 10. The anesthetic compound is more soluble in the wall material of the tube than in water so that it will not be washed out of the wall material by aqueous fluids in the body passage. Anesthetic compounds having suitable solubilities are lidocaine base:

2(Diethylamino)-N-(2,6-dimethyl-phenyl)acetamide, and dibucaine base:

2-Butoxy-N-[2-(diethylamino)ethyl]-4-quinolinecarboxamide.

These compounds are additionally advantageous in that they are not affected by conventional sterilization techniques which involve exposure to ethylene oxide.

The method of manufacture of tubes according to the invention is illustrated in the following examples.

EXAMPLE 1

A #16 urethral catheter made of polyvinyl chloride was placed in a large glass chamber together with 10 grams of lidocaine base. The lidocaine base was contained in a watch glass physically separated from the catheter. The glass chamber was evacuated to about 0.001 mm. Hg and placed in an oven maintained for 12 hours at 77 deg. C. At the end of the 12 hour period the catheter was removed from the chamber and weighed. It had not changed in appearance, but had gained 550 mg. in weight. When the catheter was held against the tongue and lips, the area of contact developed marked numbness that became evident after 5 minutes and persisted for at least 15 minutes. The catheter was then sterilized in ethylene oxide sterilant, and aerated according to a standardized hospital procedure. After this it was inserted in a patient's urethra (with substantial discomfort) and taped in place. After about 3 minutes the discomfort abated markedly, and the catheter could be moved about without problem. The catheter was left in place for eight hours without discomfort. There was no pain on removal; or any usual sequela.

EXAMPLE 2

A solution of 20% dibucaine base in food grade ethyl acetate was prepared. Fifteen #7 endotracheal tubes made of polyvinyl chloride were dipped in this solution to coat the outer surfaces with the solution. The coated tubes were then baked at 77 deg C for 12 hours to drive off the ethyl acetate and dissolve the dibucaine base into the wall material of the tubes. The tubes were then sterilized with ethylene oxide, and aerated according to standard hospital practice. The tubes emerged from the process without any change in appearance. A tube thus treated when held against the tongue for 5 minutes produced a marked numbness on the contacted areas which lasted for 45 minutes. Ten of these tubes were introduced into the trachea of dogs in connection with surgical procedures. The person who performed the surgical procedures noted that when using the treated tubes there was less coughing and chewing on the endotracheal tubes than when conventional tubes were used in similar procedures, and also noted that the animals remained asleep with lower concentrations of general anesthetic agent. None of the animals suffered from any sequela that could be noted.

EXAMPLE 3

Ninety five grams of pellets of vinyl-urethane copolymer (Vythene, Dexter Chemical) and 5 grams of dibucaine base were baked at 93 deg C for 12 hours with occasional stirring. This process incorporated the dibucaine base into the material of the pellets. Three grams of these treated pellets were further treated by pressing between two metal plates held at 171 degrees C in vacuum to create a sheet of film about 0.25 mm thick. A sheet of film emerged that was clear, elastic, and very strong. It is believed that the pressing operation simulates the mixing and working of such pellets when they are extruded in a conventional processing for making intubation devices. A piece of this film was tested on the tongue and lips and found to have strong anesthetizing properties. Numbness started to develop in 5 minutes, peaked in intensity in 15 minutes, and persisted for at least 45 minutes. A piece of the film was soaked in 38 degree C water for 24 hours. It is believed that this soaking procedure simulates the exposure of a tube to aqueous fluids during emplacement in a body passage. At the end of the soaking period the film was again tested on the tongue and lips and exhibited anesthesizing effects as before, but with a slower onset and somewhat diminished intensity.

EXAMPLE 4

Ten grams of lidocaine base and 90 grams of vinyl-urethane copolymer pellets were baked with agitation at 93 degrees C for 12 hours. At the end of this treatment the pellets stuck firmly to one another. After cooling, the pellets were broken apart, and 3 grams were pressed at 171 degrees C into a film about 0.25 mm thick. The film was clear, elastic, and tough. When a piece of this film was held on the tongue, intense numbness developed after 5 minutes and persisted for at least 15 minutes. After soaking the film in 38 degree C water for 24 hours, a test against the tongue showed a numbing effect but at a diminished level. Two hours after the soaking, the film again had strong numbing properties.

EXAMPLE 5

A solution of 30% lidocaine base in ethyl acetate was prepared. A #14 naso-gastric tube made of polyvinyl chloride was coated by dipping in this solution. The coated tube was then baked for 12 hours at 77 degrees C to drive off the ethyl acetate and incorporate the lidocaine base into the tube material. The tube was then passed into a subject's stomach through the nose (with substantial discomfort because of the marked sensitivity of the nose plus problems with the gag reflex). Initially after introduction of the tube, any movement of the tube caused sharp pain in the nasal passage and induced gagging. After a few minutes had passed, the tube could be manipulated without causing gagging or discomfort. The tube was taped in place, left for 12 hours, and removed without disturbing sensations. When tested later on the tongue and lips, numbing effect was still present, although in lowered intensity.

What is claimed is:

1. A tube for introduction into a body passage of an animal for medical purposes, said tube having a wall with an inner surface defining an interior lumen, the wall having an outward facing surface which, when the tube is emplaced in a body passage of an animal, contacts body tissue of the animal, the wall of said tube being composed of wall material having dissolved therein a topical anesthetic compound, the topical anesthetic compound being more soluble in the wall material than in water, the concentration of anesthetic compound in the wall material being such that when the tube is emplaced in and in contact with an animal's body passage, anesthetic compound diffuses to a surface of the body passage in contact with the tube at a rate to be effective in maintaining anesthesia.

2. A tube as claimed in claim 1, wherein said topical anesthetic compound is unreactive with ethylene oxide as used in sterilizing procedures.

3. A tube as claimed in claim 1, wherein said wall is composed entirely of a single polymeric wall material.

4. A tube as claimed in claim 3, wherein said wall material is polyvinyl chloride.

5. A tube as claimed in claim 3, wherein said wall material is vinyl-urethane copolymer.

6. A tube as claimed in claim 4, wherein said topical anesthetic compound is unreactive with ethylene oxide as used in sterilizing procedures.

7. A tube as claimed in claim 6, wherein said topical anesthetic compound is base.

8. A tube as claimed in claim 6, wherein said topical anesthetic compound is base.

9. A tube as claimed in claim 5, wherein said topical anesthetic compound is unreactive with ethylene oxide as used in sterilizing procedures.

10. A tube as claimed in claim 9, wherein said topical anesthetic compound is base.

11. A tube as claimed in claim 9, wherein said topical anesthetic compound is base.

* * * * *

UNITED STATES PATENT AND TRADEMARK OFFICE
CERTIFICATE OF CORRECTION

PATENT NO. : 5,279,594
DATED : January 18, 1994
INVENTOR(S) : Richard R. Jackson It is certified that error appears in the above-indentified patent and that said Letters Patent is hereby corrected as shown below:

Col. 4, line 33; insert --lidocaine-- before "base";

Col. 4, line 35; insert --lidocaine-- before "base";

Col. 4, line 40, insert --lidocaine-- before "base";

Col. 4, line 42, insert --lidocaine-- before "base".

Signed and Sealed this

Thirtieth Day of May, 1995

Attest:

BRUCE LEHMAN

*Attesting Officer*  *Commissioner of Patents and Trademarks*